US011904132B2

(12) United States Patent
Otten et al.

(10) Patent No.: US 11,904,132 B2
(45) Date of Patent: Feb. 20, 2024

(54) PACKAGING FOR A MEDICAMENT CONTAINER

(71) Applicant: Sanofi, Paris (FR)

(72) Inventors: Martin Otten, Frankfurt am Main (DE); Sebastian Thiel, Frankfurt am Main (DE); Daniel Wagner, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 17/253,305

(22) PCT Filed: Jun. 24, 2019

(86) PCT No.: PCT/EP2019/066575
§ 371 (c)(1),
(2) Date: Dec. 17, 2020

(87) PCT Pub. No.: WO2020/002178
PCT Pub. Date: Jan. 2, 2020

(65) Prior Publication Data
US 2021/0369945 A1    Dec. 2, 2021

(30) Foreign Application Priority Data

Jun. 25, 2018  (EP) ..................................... 18305805

(51) Int. Cl.
*A61M 5/00* (2006.01)
(52) U.S. Cl.
CPC ................................... *A61M 5/002* (2013.01)
(58) Field of Classification Search
CPC .................................................... A61M 5/002
(Continued)

(56) References Cited

U.S. PATENT DOCUMENTS 2,366,053 A * 12/1944 Putter ............... A61M 37/0069
206/530
2,525,958 A * 10/1950 Seager ................... B65D 51/26
206/530

(Continued)

OTHER PUBLICATIONS

PCT International Preliminary Report on Patentability in International Application No. PCT/EP2019/066575, dated Dec. 29, 2020, 7 pages.

(Continued)

*Primary Examiner* — Jacob K Ackun
(74) *Attorney, Agent, or Firm* — Fish & Richardson P.C.

(57) ABSTRACT

The present disclosure relates to a packaging for a medicament container, wherein the medicament container comprises at least one distal container abutment section and at least one proximal container abutment section, the packaging comprising: a bottom and a sidewall structure connected to the bottom, the bottom and the sidewall structure confining a storage space configured to accommodate at least one medicament container, at least one distal packaging abutment section, and at least one proximal packaging abutment section, wherein the at least one distal packaging abutment section is integrated into or arranged at one of the sidewall structure and the bottom and configured to abut with the at least one distal container abutment section, wherein the at least one proximal packaging abutment section is integrated into or arranged at the sidewall structure and configured to abut with the at least one proximal container abutment section.

14 Claims, 4 Drawing Sheets (58) Field of Classification Search
USPC .............. 206/364, 365, 528, 530, 521, 591
See application file for complete search history.

(56) References Cited

U.S. PATENT DOCUMENTS

| | | | |
|---|---|---|---|
| 3,439,796 A | 4/1969 | Zykoski | |
| 3,489,268 A | 1/1970 | Meierhoefer | |
| 3,819,081 A * | 6/1974 | Runte | B65D 41/04 206/592 |
| 4,114,759 A * | 9/1978 | Maloney, Jr. | B29C 45/0025 206/508 |
| 4,159,764 A * | 7/1979 | Schinke | F42B 39/00 206/583 |
| 4,284,196 A * | 8/1981 | Lagerkvist | F42B 3/28 229/940 |
| 4,460,090 A * | 7/1984 | Paoletti | A61J 1/03 220/721 |
| 4,753,345 A | 6/1988 | Goodsir et al. | |
| 5,316,146 A * | 5/1994 | Graff | A61B 10/0096 D24/227 |
| 5,318,183 A * | 6/1994 | Cohen | B65D 77/0493 215/6 |
| 5,590,782 A * | 1/1997 | Haber | A61J 1/16 220/663 |
| 6,793,076 B1 * | 9/2004 | Luo | B65D 77/0493 206/592 |
| 8,708,196 B2 * | 4/2014 | Spitz | B65D 85/42 222/129 |
| 8,734,420 B2 * | 5/2014 | Ariagno | A61J 1/16 206/370 |
| 9,333,289 B1 * | 5/2016 | Hirschmann | A61M 5/002 |
| 9,505,527 B1 * | 11/2016 | Campbell | A47G 19/2205 |
| 2007/0272581 A1 * | 11/2007 | Guelker | B65D 23/0885 206/521 |
| 2010/0181218 A1 * | 7/2010 | Beccaro | A61L 2/07 604/218 |
| 2010/0300922 A1 * | 12/2010 | Gilad | A61B 1/00144 206/530 |
| 2012/0080351 A1 * | 4/2012 | Takahashi | B65D 25/101 206/528 |
| 2013/0062245 A1 * | 3/2013 | Folchini | A61M 5/002 493/162 |
| 2014/0078854 A1 * | 3/2014 | Head | B01F 31/20 206/364 |
| 2017/0008686 A1 * | 1/2017 | Tanoguchi | B65D 75/326 |
| 2017/0367780 A1 * | 12/2017 | Van Der Raad-Meijer | B65D 75/366 |
| 2018/0085515 A1 * | 3/2018 | Mide | B65D 75/366 |

OTHER PUBLICATIONS

PCT International Search Report and Written Opinion in International Application No. PCT/EP2019/066575, dated Sep. 26, 2019, 9 pages.

* cited by examiner

PACKAGING FOR A MEDICAMENT CONTAINER

CROSS REFERENCE TO RELATED APPLICATIONS

The present application is the national stage entry of International Patent Application No. PCT/EP2019/066575, filed on Jun. 24, 2019, and claims priority to Application No. EP 18305805.6, filed on Jun. 25, 2018, the disclosures of which are incorporated herein by reference.

TECHNICAL FIELD

The present disclosure relates to the field of packaging for medicament containers, such as cartridges, carpules, vials or prefilled syringes. In particular, the disclosure relates to a secondary packaging configured to accommodate a primary packaging for a liquid medicament. The primary packaging, such as a cartridge, a vial, a carpule or a pre-filled syringe is typically filled with a liquid medicament, e.g. with an injectable liquid medicament. The secondary packaging is configured to accommodate the primary packaging serving as a medicament container. In a further aspect the disclosure relates to a packing for at least one medicament container, wherein the packaging is provided with a medicament container assembled therein.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such as diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a holder, e.g. a cartridge holder configured to receive a medicament container, e.g. in form of a cartridge at least partially filled with the medicament to be expelled. The device further comprises a drive mechanism, usually having a displaceable plunger or piston rod to operably engage with a bung or piston of the medicament container or cartridge. By means of the drive mechanism and the piston rod, the bung or piston of the cartridge is displaceable in a distal direction or dispensing direction and may be therefore configured to expel a predefined amount of the medicament via a piercing assembly, e.g. in form of an injection needle, connected to or releasably connectable with an outlet end of the medicament container.

With reusable drug delivery devices an empty cartridge is replaceable by a filled one. In contrast to that, drug delivery devices of disposable type are to be entirely discarded when the medicament in the cartridge has been dispensed or used-up.

In general, medicament containers, such as cartridges, carpules or pre-filled syringes typically comprise a barrel of e.g. tubular shape having an outlet at a distal end and having a bung or a piston movably arranged inside the barrel. The bung or piston seals the barrel towards a proximal end opposite to the distal outlet end. By displacing the bung towards the distal end a predefined amount of the medicament, i.e. a dose of the medicament, can be expelled through the outlet of the barrel.

For use with a drug delivery device, e.g. for use with an injection device but also for manual use it is of benefit, that the position of the bung remains stationary during storage and transportation, i.e. after the medicament container has been released by a pharmaceutical manufacturer and before the medicament container is actually used by a patient or care giver. With pen-type injectors, auto injectors, injection pumps or prefilled syringes it is required, that the bung of the medicament container is and remains stationary at a predefined position in the barrel. An accurate axial or longitudinal position of the bung or piston inside and relative to the barrel of the medicament container is of importance especially for drug device combinations, i.e. for drug delivery devices, such as injection devices readily equipped with such a medicament container. For some applications it may be desirable, that the bung is slidably movable inside the barrel under rather moderate or low forces applied to the bung. Hence, a friction coefficient between the bung and an inside surface of the sidewall of the barrel should be rather low. Yet, a rather low break loose force between the bung and the barrel may also be required for some application purposes or drug device combinations.

On the one hand a friction coefficient, e.g. a static friction and/or a sliding friction between the bung and the barrel can be modified in many different ways, such as by selecting an appropriate elastic material for the bung and/or by modifying the geometry of the bung. On the other hand a reduced friction between the bung and the barrel may come along with the disadvantage that the bung may rather easily become subject to a movement relative to the barrel during transportation and storage of the cartridge. Inevitable and minor variations of a storage temperature may lead to a thermal expansion of the medicament thus exerting a pressure to the bung in proximal direction. Moreover, the entire medicament container may be subject to mechanical shock or vibrations during transportation. Such external conditions may induce a movement of the bung towards the proximal end of the barrel. In a worst case the bung may even protrude from the barrel or may slide out of the barrel. This may compromise the sterility of the medicament container.

SUMMARY

This specification describes a packaging for a medicament container that serves to prevent an uncontrolled movement of the bung or piston of the medicament container even if the medicament container and the packaging are subject to mechanical shock, vibrations or varying thermal conditions. The packaging described in the specification is easy to manufacture at a low cost, and intuitive and straightforward to use.

In one aspect there is provided a packaging for a medicament container. The packaging is particularly dedicated for medicament containers configured to be filled with a liquid medicament. The packaging is particularly dedicated and configured for medicament containers comprising a barrel and a bung or piston. The bung or piston is arranged inside the barrel and the barrel has an outlet at a distal end.

The bung is movably arranged inside the barrel and seals the barrel towards a proximal end. The barrel is filled with a liquid medicament. The liquid medicament can be expelled from the interior of the barrel through the outlet of the barrel by moving or urging the bung or piston in a distal direction thereby increasing the fluid pressure inside the interior volume of the barrel thus urging an amount of the medicament through the outlet.

The medicament container further comprises at least one distal container abutment section facing in the distal direction, i.e. towards the distal end of the barrel. The medicament container further comprises at least one proximal container abutment section facing in the proximal direction. The distal container abutment section may be located at a distal end of the container but may also be located longitudinally offset from the distal end of the container. The same is valid for the proximal container abutment section. It may be located at a proximal end of the container or may be located longitudinally offset from the proximal end of the container.

The packaging is particularly dedicated and designed for receiving and accommodating a medicament container as described above. The packaging comprises a bottom and a sidewall structure. The sidewall structure is connected to the bottom. The bottom and the sidewall structure confine a storage space configured to accommodate at least one medicament container. The storage space formed by the bottom and the sidewall structure may also be configured to accommodate numerous or a series of medicament containers of equal or of different shape and/or size.

The packaging comprises at least one distal packaging abutment section that is integrated into one of the sidewall structure and the bottom or which distal packaging abutment section is arranged at one of the sidewall structure and the bottom. The distal packaging abutment section is configured to abut with the at least one distal container abutment section when the medicament container is located inside the storage space.

The packaging further comprises at least one proximal packaging abutment section that is integrated into the sidewall structure or arranged at the sidewall structure. The at least one proximal packaging abutment section is configured to abut with the at least one proximal container abutment section when the medicament container is located inside the storage space.

The distal packaging abutment section typically faces in proximal direction to engage or to abut with the distally facing distal container abutment section. The proximal packaging abutment section typically faces in distal direction so as to engage or to abut with the proximal container abutment section.

In typical configurations and with typical examples the distal container abutment section is provided at a distally facing and radially widened shoulder portion of the barrel or at a distal end, e.g. at the distal end face of the barrel or outlet of the medicament container. The proximal container abutment section is typically provided at a proximal end of the barrel or at a proximal end of the bung or piston located inside the barrel. In either way and since the distal and the proximal container abutment sections are in abutment or engagement with correspondingly shaped distal and proximal packaging abutment sections as the medicament container is inserted into the storage space an uncontrolled movement of the bung or piston out of the barrel in proximal direction can be effectively blocked and prevented.

The proximal packaging abutment section, which is either in axial abutment with the proximal end of the barrel or which is in direct abutment with a proximal side or proximal face of the bung prevents an uncontrolled movement of the bung towards the proximal direction relative to the barrel.

The sidewall structure of the packaging comprises a distal sidewall section and a proximal sidewall section. The storage space is confined by the distal sidewall section and the proximal sidewall section at least with regard to the axial or longitudinal direction of the packaging. Here, the longitudinal direction of the packaging coincides with the longitudinal geometry or longitudinal or axial elongation of the medicament container. If the packaging is configured to receive numerous medicament containers that are, e.g. arranged next to each other, the size of the distal sidewall section and the proximal sidewall section may be even larger than the size of lateral sidewall sections, e.g. a left sidewall section and a right sidewall section extending between distal and proximal sidewall sections.

For reasons of a consistent and uniform description of the packaging the distal sidewall section of the packaging is that sidewall section that faces towards the distal end of the medicament container or medicament containers and the proximal sidewall section of the packaging is that sidewall section that is located opposite to the distal sidewall section. The proximal sidewall section of the packaging faces towards the proximal end of the medicament container or the medicament containers.

The at least one proximal packaging abutment section is integrated into or is arranged at the proximal sidewall section. The proximal packaging abutment section may coincide with a planar shaped proximal sidewall section. Insofar, an effective longitudinal size of the storage space may be defined by the length of the empty space between the inside surfaces of the distal sidewall section and the oppositely located proximal sidewall section. With some examples the effective longitudinal size of the storage space, e.g. the inner distance between the distal sidewall section and the proximal sidewall section substantially matches with the overall longitudinal extension of the medicament container.

Upon inserting the medicament container into the storage space the distal container abutment section engages or abuts with an inside of the distal sidewall section and a proximal container abutment section, e.g. the proximal end of the barrel of the medicament container engages or abuts with the proximal sidewall section of the packaging. In this way, the medicament container can be longitudinally or axially clamped or squeezed in the storage space of the packaging. The medicament container will be hence hindered to move in longitudinal direction inside the packaging if the packaging should become subject to mechanical shock or vibrations. Moreover, the abutment of the proximal packaging abutment section with the proximal container abutment section prevents an undesired displacement or movement of the bung in proximal direction out of the barrel.

The at least one proximal packaging abutment section is integrated into or is arranged at an inward facing side of the proximal sidewall section. The proximal packaging abutment section comprises a protrusion or projection protruding from the inward facing side into the storage space. The inwardly facing protrusion may be configured to engage or to abut with one of the proximal end of the barrel or the proximal end of the bung located inside the barrel. It may not be necessary that the proximal packaging abutment section is or gets in direct abutment with the proximal container abutment section upon insertion of the medicament container into the storage space. A small gap may be allowed between the protrusion of the proximal packaging abutment section and the proximal container abutment section.

The protrusion is typically dimensioned and shaped such that a gap between the protrusion and the proximal container abutment section is smaller than an insertion depth ID or smaller than the axial length of the bung LB. Here, the insertion depth ID is defined by the longitudinal or axial distance between a distal end face of the bung and a proximal end of the barrel of the medicament container.

It may be less than or equal to half of the total axial or longitudinal elongation of the insertion depth ID or axial length of the bung LB. In this way the bung is allowed to move a certain extent towards the proximal end of the barrel. In an extreme situation the bung may even slightly protrude from the barrel. In any case the protrusion of the proximal packaging abutment section is shaped such that the bung is hindered to move out of the barrel of the medicament container.

With other examples the protrusion is sized to bridge a gap between the proximal packaging abutment section and the proximal container abutment section. The protrusion may be sized to abut with the proximal container abutment section when the medicament container is located inside the storage space. Optionally and when arranged inside the storage space the distal container abutment section is in abutment with the distal packaging abutment section. When arranged inside the storage space the distal container abutment section may be in abutment with the distal packaging abutment section and the proximal container abutment section may be in abutment with the proximal packaging abutment section.

With another example the protrusion of the at least one proximal packaging abutment section comprises a cross-section that is larger than or equal to a cross-section of the barrel at the proximal end of the barrel. Since the protrusion comprises a diameter or cross-section exceeding the diameter or cross-section of the barrel the protrusion is configured to provide a proximal end stop for the barrel as such. The protrusion is configured to engage or to abut with the proximal end of the barrel. The barrel may be open-ended towards its proximal end and having the bung located inside is hence entirely covered and/or closed by the protrusion as the medicament container is inserted into the storage space. In this way a proximally directed movement of the bung relative to the barrel is limited to a position of the bung flush with the proximal end of the barrel. The bung cannot protrude from the barrel as the proximal end of the barrel is in abutment with the protrusion of the proximal packaging abutment section.

According to another example the protrusion of the proximal packaging abutment section comprises a cross-section that is smaller than a cross-section of the barrel at the proximal end of the barrel. Typically, the protrusion of the proximal packaging abutment section is arranged radially overlapping with the storage space occupied by the medicament container when inserted into the packaging. In this way and since the protrusion is sized and configured to enter the barrel from the proximal end. It may hence protrude into the proximal end of the barrel and may thus limit an eventual proximally directed movement of the plunger relative to the barrel. The proximal packaging abutment extending distally into the proximal end of the barrel may directly engage or abut with the proximal side of the bung or piston. In other examples there may be provided a small gap between a free end of the protrusion and a proximal end face of the bung. With this example the bung is hindered by the proximal packaging abutment section to move proximally and to reach a configuration in which its proximal end face flushes with a proximal end of the barrel.

A protrusion having a diameter or cross-section smaller than a cross-section of the barrel may even get in direct mechanical abutment or contact with the bung as the medicament container is inserted into the packaging. Then, a proximally directed movement of the bung relative to the barrel is effectively blocked. Typically, the protruding proximal packaging abutment section is coaxially arranged to the tubular-shaped barrel of the medicament container when located inside the packaging. In this way, the protrusion of the proximal packaging abutment section may engage with a radial center of the bung thus applying a rather symmetric counterforce to the bung configured to prevent a proximally directed movement thereof relative to the barrel.

In a further example the protrusion of the proximal packaging abutment section comprises a base portion and a free end portion. The base portion is located between the free end portion and the proximal sidewall section of the sidewall structure. Typically, the base portion and the free end portion are integrally formed. The base portion comprises a first cross-section and the free end portion comprises a second cross-section. The second cross-section is smaller than the first cross-section. In other words, the base portion comprises a larger diameter or cross-section compared to the free end portion. The diameter or cross-section of the base portion may be larger than or equal to the diameter or cross-section of the barrel of the medicament container.

The diameter or cross-section of the free end portion is typically smaller than the diameter or cross-section of the barrel. In this way the free end portion may directly engage with the proximal end of the piston located inside the barrel and being located distally offset from the proximal end of the barrel while the base portion can get in direct abutment with the proximal end of the barrel. With some examples the free end portion is a step down extension of the base portion. At the interface between the free end portion and the base portion the base portion may comprise a distally facing abutment shoulder to engage with the proximal end of the barrel.

With the base portion and the free end portion the proximal packaging abutment section may provide a twofold function. The base portion may be in abutment with the barrel of the medicament container and may hence delimit or block a proximally directed motion of the barrel inside and relative to the packaging. At the same time or alternative, the free end portion of the protrusion engages with the proximal side of the bung or delimits or blocks a respective movement of the bung relative to the packaging and/or relative to the barrel of the medicament container.

With another example the protrusion of the proximal packaging abutment section comprises one of a tapered, a bulged and a convex shaped geometry. Depending on the specific geometry the proximal packaging abutment section is configured to engage or to abut with one or both of the proximal end of the barrel and a proximal end face or proximal end of the bung located inside the barrel. A tapered, bulged or convex shaped geometry of the protrusion is of particular benefit to provide and to enable a direct axial abutment between the protrusion and the proximal side of the bung because the proximal end of the bung is typically located distally offset from a proximal end of the barrel of the medicament container.

In another example at least one of the sidewall structure and the bottom comprises a flange section protruding inwardly into the storage space. The flange section then forms a distal packaging abutment section. The flange section may be located closer to the distal sidewall section than to the proximal sidewall section. The flange section may protrude inwardly from a left or right sidewall or may protrude upwardly from the bottom of the packaging. If the packaging comprises a lid or ceiling portion the flange section may also protrude downwardly and inwardly from the lid or ceiling portion.

The flange is typically configured to engage with a neck portion of the medicament container. The medicament container typically comprises a head forming the distal outlet end of the medicament container. The head is connected via a neck to the bottle-shaped or tubular-shaped proximal portion of the barrel. The neck radially widens towards the proximal direction and merges into a shoulder portion extending into the tubular section of the barrel. Typically, the flange section of the packaging is configured to abut with a distally facing shoulder section of the barrel. Here, the proximal side of the inwardly protruding flange section forms the distal packaging abutment section. The distally facing shoulder portion of the barrel forms the distal container abutment section to axially abut or to axially engage with the flange section as the medicament container is inserted into the packaging.

The flange section may be provided exclusively or in addition to the distal sidewall section of the packaging also forming a distal packaging abutment section. Hence, the packaging may comprise two or even more distal packaging abutment sections. A first distal packaging abutment section may be provided by an inside surface of the distal sidewall section and a second distal packaging abutment section may be provided by the flange section. In this way, a twofold distally directed abutment between the barrel and the packaging can be provided.

Typically and when the barrel is made of a vitreous material the shape and position of the radially widening shoulder may be subject to geometric variations and tolerances. By having a first and a second distal packaging abutment section such geometric tolerances of the barrel can be leveled out or compensated for. The flange section may be flexible to a certain degree with regard to a distally directed or proximally directed deformation. In this way the medicament container can be in principle biased in proximal direction and towards the proximal packaging abutment section as the medicament container is inserted into the storage space.

With another example the flange section may be arranged and configured to engage a proximally facing flange section of a head portion of the barrel of the medicament container. A medicament container such as a cartridge filled with a medicament and provided with a beaded cap and a septum at its distal end typically comprises a pierceable head section forming the distal outlet of the medicament container that transitions or merges in proximal direction into the radially narrowed neck. The flange section of the packaging may be arranged at a distance from the distal sidewall section of the sidewall structure that matches with the axial or longitudinal extension of the head section of the medicament container. Here, the flange section may provide a second proximal packaging abutment section to engage or to abut with the proximally facing indented portion of the head of the medicament container.

In another example the bottom and the sidewall structure and optionally further components of the packaging, such as a lid or closure, comprise a thermoplastic material. In particular, the bottom and the sidewall structure and optionally further components of the packaging may be made of a thermoplastic material. The packaging may be manufactured by a thermoforming of a thermoplastic material or by an injection molding process. Here, the proximal packaging abutment sections as well as distal packaging abutment sections can be easily integrated into the structure of the bottom and/or of the sidewall structure. For this only an existing mold has to be modified so that the bottom and/or the sidewall structure is provided with at least one proximal and/or distal packaging abutment section, which abutment section comprises at least one of a protrusion or a flange section to engage with a distal and/or proximal container abutment section of the medicament container. Manufacturing of the packaging on the basis of a thermoplastic material offers a rather cost efficient mass manufacturing process.

According to another example the bottom and the sidewall structure and further optional components of the packaging, such as a closure or a lid, comprises a foldable cardboard material. The entire packaging may even be made of a foldable cardboard material. Here, the packaging abutment sections may be provided as foldable sections of a cardboard blank. Upon folding a cardboard blank to constitute the packaging the packaging abutment sections may be provided by folding. The flange section and/or the protrusion of the proximal packaging abutment section may be provided as foldable portions of a cardboard blank. They may be folded inwardly and into the storage space upon assembly or preparation of the packaging from a cardboard blank.

Also, an outwardly bulged folded portion may be provided near or at at least one of the distal sidewall section and the proximal sidewall section of the sidewall structure. The outwardly bulged or folded portion of the sidewall sections may be configured for becoming turned inwardly, even after insertion of the medicament container into the storage space. In this way at least one of the proximal and distal packaging abutment sections may be formed by turning an outwardly protruding portion of a sidewall into an inwardly protruding portion of the sidewall to form a packaging abutment section.

Such a reconfigurable packaging may be beneficial in such cases where an inwardly protruding protrusion, e.g. of the proximal packaging abutment section would hinder insertion of the medicament container into the storage space.

According to another example at least one of the distal packaging abutment section and the proximal packaging abutment section is integrally formed with at least one of the sidewall structure and the bottom. The integration of the packaging abutment sections into the sidewall structure and/or into the bottom is beneficial in that the packaging may then comprise a single piece packaging. This is of particular advantage for arranging at least one or numerous medicament containers into the packaging and when a large number of equally sized or equally shaped medicament containers have to be packed inside a packaging. The integration of the packaging abutment sections into the bottom and/or into the sidewall structure is further beneficial in terms of a cost efficient mass manufacturing of the packaging.

With another example at least one of the distal packaging abutment section and the proximal packaging abutment section is integrated into an insert that is provided as a separate piece. The insert is insertable into the storage space of the packaging but might be detached or removed from the packaging. The insert and the packaging may comprise mutually corresponding fasteners thus supporting a fixing of the insert inside the storage space of the packaging. With the insert the sidewall structure or the bottom of the packaging may be void of packaging abutment sections and may be thus void of the flange section or of an inwardly extending protrusion to engage or to abut with a container abutment section.

However, the insert allows retrofitting of an existing packaging with dedicated packaging abutment sections without modifying the overall design of an existing packaging. Moreover, the insert may be particularly designed and configured for a particular type of medicament containers. It is for instance conceivable, that medicament containers with equally shaped barrels are filled to a different degree with a medicament. This results in a varying position of the bung inside the barrel. Here, differently shaped inserts may be appropriately used for differently configured medicament containers, e.g. having different filling levels.

For medicament containers having a rather small filling volume that comes along with a comparatively large longitudinal offset of the bung from the proximal end of the barrel the protrusion of the insert may be comparatively long. With medicament containers comprising a comparatively large filling level the axial or longitudinal offset between a proximal end of the bung and the proximal end of the barrel may be comparatively small. For such medicament containers the protrusion provided on or by the insert is comparatively short.

In one example the insert may comprise a distance spacer to be positioned between, e.g. the proximal sidewall section of the packaging and one of a proximal end of the barrel and the bung of the medicament container. With other examples the insert comprises a bottom section and a sidewall section. Here, the bottom section of the insert is configured to be placed onto the bottom of the packaging and the sidewall section is configured to be placed on or in abutment with an inside surface of a respective sidewall of the packaging. In this way, a well-defined and precise slip-free arrangement of the insert inside the packaging can be obtained.

For instance, the insert may comprise a bottom section that comprises a longitudinal extension equal to the longitudinal extension of the bottom of the packaging. In this way and when the insert is placed inside the storage space on the bottom of the packaging a distal end of the insert is in abutment with a distal sidewall section and a proximal end of the bottom section of the insert is in axial abutment with a proximal sidewall section of the packaging. In this way, a longitudinal movement of the insert relative to the packaging is effectively blocked and impeded.

An upwardly folded sidewall section of the insert, e.g. a proximal sidewall section of the insert may be provided with a distally extending protrusion to form the proximal packaging abutment section. The proximal packaging abutment section provided by the insert may abut or engage with at least one of the proximal end of the barrel and a proximal end of the bung.

With a further example there is provided a packaging as described above, wherein at least one medicament container is arranged inside the storage space of the packaging. The medicament container comprises a barrel and a bung. The bung is arranged inside the barrel. The barrel has an outlet at a distal end and the bung is movably arranged inside the barrel. The bung seals the barrel towards the proximal end of the barrel. The barrel is filled with a liquid medicament. The medicament container comprises at least one distal container abutment section facing in the distal direction and the container further comprises at least one proximal container abutment section facing in the proximal direction.

When arranged inside the storage space the at least one distal packaging abutment section is in abutment with the at least one distal container abutment section. Additionally or alternatively the at least one proximal packaging abutment section is in abutment with the at least one proximal container abutment section. In this way, the medicament container is hindered to move in distal direction or in proximal direction when arranged inside the packaging. Even both, the distal and the proximal packaging abutment sections may be in direct abutment with the at least one distal and proximal container abutment sections, respectively. In such a configuration, the medicament container is clamped or squeezed in longitudinal or axial direction inside the packaging. In any case the proximal packaging abutment section is configured to engage or to abut with at least one of the proximal end of the barrel or of the bung of the medicament container. In this way the bung is hindered from moving out of the barrel if the packaging assembly with the medicament container located therein should become subject to mechanical shock or vibrations.

According to a further example the distal container abutment section is located at a distal end face of the medicament container or at a distally facing shoulder section of the barrel. The distal container abutment section is configured to axially abut with a distal packaging abutment section so as to block or to impede a distally directed motion of the medicament container inside the packaging.

In a further example the proximal container abutment section is located at a proximal end face of the barrel, at a proximal end face of the bung or at a proximal end of a spacer connected to the bung. The spacer may comprise a plunger detachably connected to the proximal end of the bung or integrally formed with the bung. With some examples the proximal container abutment section may be located at a proximally facing indented portion of a head located at a distal end of the medicament container.

The head portion of the barrel, the proximal end of the barrel, the proximal end face of the bung and a proximal end of a plunger connected to the bung may serve as a proximal container abutment section that is configured to axially abut or mechanically engage with a correspondingly-shaped proximal packaging abutment section. In this way, a proximally directed movement of the container relative to the packaging and/or a proximally directed movement of the bung relative to the barrel or relative to the packaging can be effectively prevented.

The medicament container may be designed or implemented as a cartridge for insertion into an injection device, such as a mechanically implemented handheld pen-type injector, an auto injector or in a mechanically and/or electrically operated injector or injection pump.

With other examples the medicament container is a prefilled syringe, wherein the bung is formed by a plunger protruding from the proximal end of the barrel.

The plunger may even be integrally formed with the bung. The plunger and the bung may form a plunger of a prefilled syringe. Here, the barrel forms or is a syringe barrel filled with a medicament and the plunger bung assembly is manually movable into the barrel in distal direction for expelling of the medicament from a distal outlet of the syringe barrel.

According to another example an effective longitudinal size $L1$ of the storage space defined by a distance between the distal packaging abutment section and the proximal packaging abutment section substantially equals or is smaller than an effective abutment size $L2$ of the medicament container plus an effective insertion depth $ID$ of the bung. The effective abutment size $L2$ of the medicament container is defined by a distance between the at least one distal container abutment section and the at least one proximal container abutment section. The insertion depth ID is defined by the longitudinal or axial distance between a distal end face of the bung and a proximal end of the barrel of the medicament container. In other words, the effective longitudinal size L1 of the storage space is defined by the following formula: L1≤L2+ID.

With a further example the effective longitudinal size L1 of the storage space is smaller than or equal to the effective abutment size L2 plus the longitudinal length or longitudinal size of the bung LB. The storage space is then defined by the following formula: L1≤L2+LB.

With other examples, the storage space may be defined by the formula L1≤L2+ID/2 or L1≤L2+LB/2.

With the examples as mentioned above or with further examples the effective longitudinal size L1 of the storage space may be equal to or larger than the effective abutment size L2 of the medicament container. With a container and a packaging fulfilling this requirement the container can be smoothly placed and inserted into the storage space of the packaging.

With these examples a limited movement of the bung towards the proximal direction relative to the barrel is allowed and supported to such an extent only that not more than 50% of the axial length of the bung protrudes from the proximal end of the barrel. That portion of the bung that may protrude from the barrel is smaller than 50% of the total longitudinal or axial length of the bung. In this way, a leak proof arrangement of the medicament container inside the storage space can still be provided.

With other examples, the effective longitudinal size L1 of the storage space is smaller than or equal to the effective abutment size L2. If the effective longitudinal size L1 is slightly smaller than the effective abutment size L2 insertion of the medicament container into the storage space is accompanied by a slight mechanical, e.g. elastic or plastic deformation of the packaging. In this way, the medicament container can be press fitted into the packaging. The effective abutment size of the medicament container can be also slightly reduced or can be slightly smaller than the effective longitudinal size of the storage space. Then, the medicament container may be press fitted or squeezed into the storage space of the packaging. Upon insertion of the medicament container into the storage space the effective abutment size L2 of the medicament container may be even slightly reduced or the medicament container might be slightly compressed in longitudinal direction.

In this way it is somehow guaranteed that the packaging comprises a well-defined effective abutment size L2. Eventual manufacturing or assembly tolerances of the medicament container, in particular in view of a longitudinal position of the bung or piston relative to the cartridge might be leveled out simply by inserting the medicament container into the storage space of the packaging. Here, the packaging may exert a distal pressure onto the bung upon insertion of the medicament container into the packaging. The bung may be subject to a slight distally directed movement as the medicament container is placed in the storage space of the packaging.

In either way and when the effective longitudinal size of the storage space corresponds to the effective abutment size it is somehow guaranteed, that the medicament container is kept stationary inside the packaging once it has been inserted into the storage space. By selecting and designing the effective longitudinal size of the storage space in accordance with the effective abutment size a slack free arrangement of the medicament container inside the packaging can be provided.

The effective longitudinal size L1 of the storage space and the effective abutment size L2 of the medicament container refer to the longitudinal or axial positions of the distal packaging abutment section and proximal packaging abutment section as well as to the axial or longitudinal position of the distal container abutment section and the proximal container abutment section. Distal and proximal packaging abutment sections may be offset in radial direction. Also the distal and proximal container abutment sections may be located at a radial offset from each other. Such radial offsets are disregarded for the determination of the effective longitudinal size of the storage space and the effective abutment size of the medicament container.

The effective longitudinal size of the storage space and the effective abutment size of the medicament container are governed by the container abutment sections and packaging abutment sections that get in mutual axial or longitudinal abutment as the medicament container is inserted into the storage space. If the distal container abutment section is located at a distal end face of the medicament container and if the proximal container abutment section is located at a proximal end of the barrel the effective abutment size will be governed by the longitudinal distance between the distal end face of the medicament container and the proximal end face of the barrel. In other situations the effective abutment size may be defined as the longitudinal distance between a shoulder portion of the barrel and a proximal end of the bung of the medicament container. It may also be defined as a longitudinal distance between a distally facing shoulder portion and the proximal end of the barrel. Moreover, the effective abutment size of the medicament container may also equal the longitudinal distance between a proximal end of the bung and a distal end face of the medicament container.

In another aspect a packaging assembly is provided including at least one medicament container comprising a barrel and a bung. The bung is arranged inside the barrel. The barrel has an outlet at the distal end and the bung is movably arranged inside the barrel and seals the barrel towards a proximal end. The barrel is filled with a liquid medicament. The medicament container comprises at least one distal container abutment section facing in distal direction. The medicament container further comprises at least one proximal container abutment section facing in the proximal direction.

The packaging assembly further includes a packaging comprising a bottom and a sidewall structure connected to the bottom. The bottom of the sidewall structure confines a storage space that is configured to accommodate at least one medicament container. The packaging further comprises at least one distal packaging abutment section integrated into or arranged at the sidewall structure. The distal packaging abutment section is configured to abut with the at least one distal container abutment section. The packaging further comprises a proximal packaging abutment section integrated into or arranged at the sidewall structure.

The at least one medicament container is arranged in the storage space. Optionally and when arranged in the storage space the at least one distal packaging abutment section abuts with the at least one distal container abutment section.

The packaging assembly further comprises at least one spacer arranged between the proximal packaging abutment section and the proximal container abutment section. The spacer is sized to bridge a gap between the proximal packaging abutment section and the proximal container abutment section when the medicament container is arranged inside the storage space of the packaging.

The spacer may belong to one of the medicament container and the packaging. The spacer may belong to the bung of the medicament container. The spacer may be detachably connected to a proximal end of the bung and may protrude from the proximal end of the bung. The spacer may be integrally formed to the bung and may protrude from a proximal end of the barrel. The spacer may comprise a plunger slidably arranged inside the barrel of the medicament container. Here, the medicament container may comprise a prefilled syringe having a plunger protruding from a proximal end of the barrel.

In a further example the spacer may be detachably or non-detachably connected to the barrel and may protrude in proximal direction from the proximal end of the barrel. When connected to the medicament container a proximal end of the spacer may form and constitute a proximal container abutment section as described above. The proximal end of the spacer is thus configured to abut with the proximal packaging abutment section as the medicament container is arranged inside the storage space of the packaging.

With other examples the spacer may be a separate part arranged inside the storage space to bridge an eventual gap between the proximal packaging abutment section and the proximal container abutment section. The longitudinal extension of the spacer comprises a length of at least 50% of the longitudinal size of the gap between the proximal packaging abutment section and the proximal container abutment section when the distal container abutment section is in abutment with the distal packaging abutment. With other examples the spacer may entirely fill the gap between the proximal packaging abutment section and the proximal container abutment section.

With some embodiments the proximal packaging abutment section coincides with an inside facing portion of a proximal sidewall section of the packaging. The proximal side wall section may be of planer and even shape. It may be void of any protrusions or recesses. With other examples, the proximal packaging abutment section comprises a protrusion protruding from the inward facing side of the proximal sidewall section into the storage space.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the scope of the invention. Further, it is to be noted, that any reference numerals used in the appended claims are not to be construed as limiting the scope of the invention.

BRIEF DESCRIPTION OF THE FIGURES

In the following, numerous examples of the container and of an injection device will be described in greater detail by making reference to the drawings, in which.

DETAILED DESCRIPTION

Figure 1:
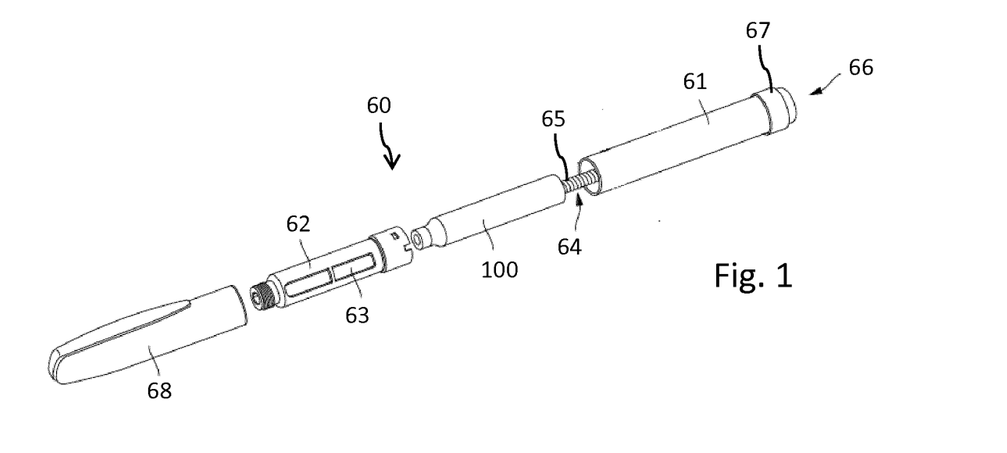
FIG. 1 shows a schematic exploded view of an injection device equipped with a medicament container.

In FIG. 1 an example of an injection device 60 is schematically illustrated. The injection device is of pen-injector type. The injection device 60 comprises a housing having a proximal housing portion 61 denoted as body and further comprising a distal housing portion 62 denoted as cartridge holder. The proximal housing portion 61 is configured to house and to accommodate a drive mechanism 64. The drive mechanism 64 comprises inter alia a piston rod 65 or a plunger. The piston rod 65 is configured to urge against a bung 104 or piston of a medicament container 100. The distal housing portion 62 comprises an inspection window 63 through which the content of the medicament container 100 can be visually inspected. Typically, the barrel 102 of the medicament container 100 is translucent so that the filling level and/or the constitution of the medicament 105 located inside the barrel 102 can be visually inspected from outside the injection device 60.

A proximal portion of the distal housing portion 62 is connectable to a distal end of the proximal housing portion 61. At the proximal end of the body 61 there is provided a dose button 66 or trigger and a dose dial 67. The dose dial 67 is configured to set a dose of a predefined size and the dose button 66 is depressible in distal direction 2 for initiating a dose expelling procedure. The distal end of the distal housing portion 62 is connectable with a double-tipped injection needle configured to penetrate a distal seal located at a distal outlet 106 of the medicament container 100. When the needle assembly (not illustrated) is detached from the distal housing portion 62 a protective cap 68 can be mounted on and over the distal housing portion 62.

The medicament container 100 as illustrated in FIG. 1 and as illustrated in the further examples of FIGS. 2-10 is a medicament cartridge having a tubular-shaped and elongated barrel 102. The barrel 102 may be made of a vitreous material, e.g. glass. The barrel 102 may be alternatively made of a pharmaceutically inert plastic material. The medicament container 100 comprises a distal end 110 provided with an outlet 106. The medicament container 100 comprises also a proximal end 112 opposite to the distal end 110. The proximal end 112 is sealed by a bung 104. The bung 104 is typically made of an elastomeric material, such as natural or synthetic rubber.

The bung 104 is slidably disposed inside the tubular-shaped interior of the barrel 102. The outlet 106 at the distal end 110 of the medicament container 100 comprises a pierceable seal 114 attached to a head portion 116 of the barrel 102. The head portion 116 extends or merges in proximal direction 3 into a narrowed neck portion 117. The neck portion 117 merges in proximal direction into a widening shoulder portion 118, which in turn extends or merges into the tubular elongated section of the barrel 102. The pierceable seal 114 is fixed to the head portion 116 by means of a beaded cap 115. The proximal end 112 of the barrel 102 is open ended. The interior of the proximal end 112 is sealed by the bung 104 or piston having a cross-section or diameter that matches and conforms with the inner diameter or cross-section of the tubular portion of the barrel 102.

The medicament container 100 comprises at least one distal container abutment section 120, 122. The distal container abutment section 120 is located at a distal end face of the medicament container 100. The distal container abutment section 120 may be formed or provided by the outlet 106 and hence by at least one of the pierceable seal 114 and the beaded cap 115. A further distal container abutment section 122 is provided by the shoulder portion 118. Both distal container abutment sections 120, 122 face in distal direction, hence towards the distal end 110 of the medicament container 100.

The medicament container 100 further comprises a proximal container abutment section 130. The proximal container abutment section 130 is formed and provided by a proximal end of the barrel 102. There may be provided a further proximal container abutment section 132. The proximal container abutment section 132 may be provided by a proximal face or a proximal portion of the bung 104.

The shoulder portion 118 and hence the distal container abutment section 122 is located proximally offset from the outlet 106, the beaded cap 115 or the pierceable seal 114 forming the further distal container abutment section 120. The proximal container abutment section 132 is located distally offset from the proximal container abutment section 130. With other examples the two proximal container abutment sections 130, 132 may be located at the same axial or longitudinal position. Hence, the proximal end of the bung 104 may flush with the proximal end of the barrel 102.

Figure 2:
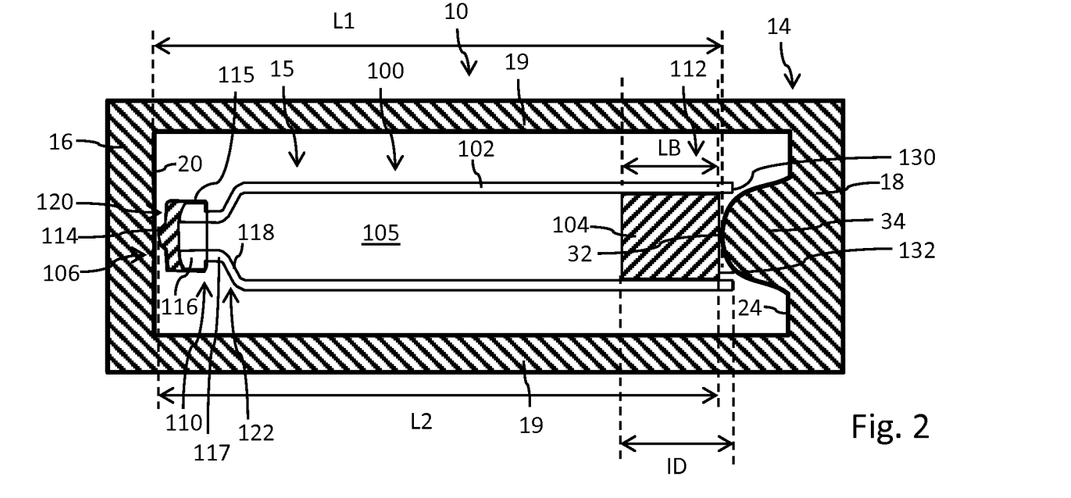
FIG. 2 is illustrative of a top view of an open packaging accommodating a medicament container.
Figure 3:
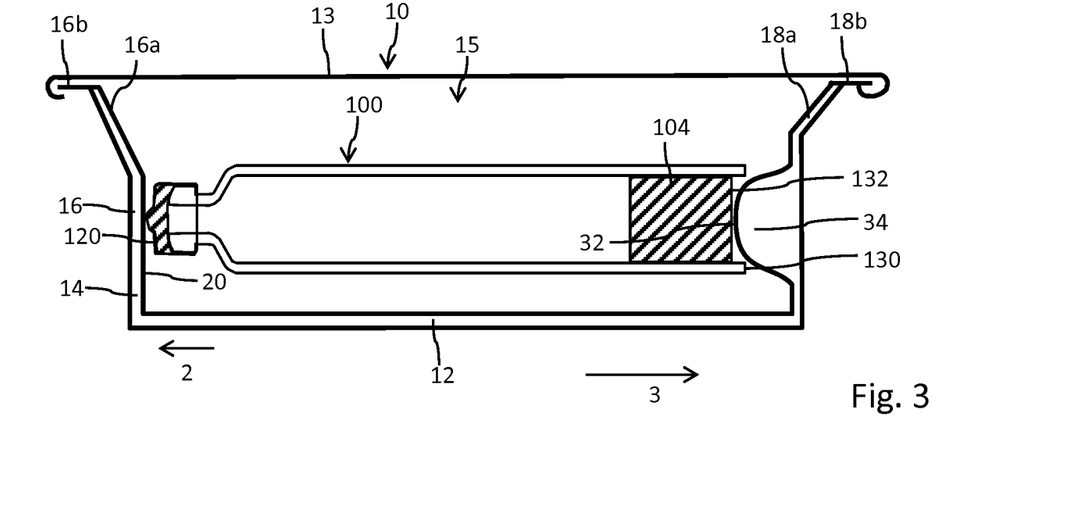
FIG. 3 shows the packaging and the medicament container according to FIG. 2 in a cross sectional side view.

The packaging 10 as illustrated in a top view in FIG. 2 and in a cross-section of FIG. 3 comprises a bottom 12 and a sidewall structure 14. The packaging 10 as illustrated in FIGS. 2 and 3 comprises a rectangular shape. The sidewall structure 14 comprises four sidewall sections, namely a distal sidewall section 16, an oppositely located proximal sidewall section 18 and two oppositely located lateral sidewall sections 19 interconnecting the distal sidewall section 16 with the proximal sidewall section 18. The sidewall sections 16, 18 and 19 are all connected and fixed to the bottom 12. The sidewall structure 14 and the bottom 12 confine a storage space 15 sized and configured to accommodate at least one medicament container 100.

At least a lower portion of the distal sidewall section 16 and of the proximal sidewall section 18 extend substantially perpendicular to the bottom 12. The packaging 10 comprises at least one proximal packaging abutment section 30, 32 that is integrated into or arranged at the sidewall structure 14 and is configured to abut with the at least one proximal container abutment section 130, 132.

The packaging 10 further comprises at least one distal packaging abutment section 20, 22 that is integrated into or arranged at the sidewall structure. The distal packaging abutment section 20, 22 is configured to abut with the at least one distal container abutment section 120, 122. With the example of FIGS. 2 and 3 the distal packaging abutment section 20 is formed and provided by an inward facing side of the distal sidewall section 16. The proximal packaging abutment section 32 is formed and provided by a protrusion 34 protruding inwardly from an inward facing side 24 of the proximal sidewall section 18 as illustrated in FIGS. 2 and 3. The distance between the distal packaging abutment section 20 and the proximal packaging abutment section 32 defines an effective longitudinal size L1 of the storage space 15.

As illustrated in FIG. 2, this effective longitudinal size L1 may be substantially equal to an effective abutment size L2 of the medicament container 100. Here, the effective abutment size L2 is defined by a longitudinal distance between the distal container abutment section 120 and the proximal container abutment section 132. In other words, the effective longitudinal size L1 of the storage space 15 substantially equals or equals the longitudinal distance between a proximal side or proximal face of the bung 104 and the distal end face 120 of the medicament container 100. When the medicament container 100 is appropriately positioned inside the storage space 15 the medicament container 100 is fixed in longitudinal direction inside the storage space 15 and the bung 104 is in abutment with the protrusion 34. In this way, the medicament container 100 and the barrel 102 are hindered to move in longitudinal direction relative to the packaging 10 and the bung 104 is hindered or prevented to move relative to the barrel 102.

Alternative to the example as illustrated in FIGS. 2 and 3 it is conceivable that there exists a gap between the proximal container abutment section 132 and the proximal packaging abutment section 32. This gap must be smaller than an insertion depth of the bung 104 with regard to the barrel 102. The insertion depth ID of the bung 104 is defined by the longitudinal distance between the distal end of the bung 104 and the proximal end of the barrel 102.

Accordingly, the effective longitudinal size L1 of the storage space is equal to or is smaller than the effective abutment size L2 of the medicament container plus the insertion depth ID of the bung 104. In this way it is effectively prevented that the bung 104 slides out of the proximal end of the medicament container 100 while accommodated inside the packaging.

According to another example the effective longitudinal size L1 of the storage space 15 is equal to or smaller than the effective abutment size L2 plus the axial elongation or size LB of the bung 104. With other examples, the storage space may be defined by the formula $L1 \leq L2+ID/2$ or $L1 \leq L2+LB/2$. Then, the bung 104 is allowed to move in proximal direction 3 relative to the barrel 102 to such an extent that no more than half of the axial elongation of the bung 104 is allowed to protrude from a proximal end of the barrel 102. Such a configuration would still provide a sufficient sealing of the interior volume of the medicament container 100.

The sidewall structure 14 as illustrated in FIG. 3, in particular at least one of the distal sidewall section 16 and the proximal sidewall section 18 comprise an outwardly extending beveled section 16a, 18a near an upper end, that is facing away from the bottom 12. At the upper end the beveled sections 16a, 18a extend into a substantially horizontally extending flange section 16b, 18b. The flange section 16b, 18b enables and provides a fastening of a closure 13. The closure 13 may comprise a foil, such as a blister foil that can be sealed or welded to the flange sections 16b, 18b. The upper end sections of the lateral sidewall sections 19 may be equally provided with respective flange sections. The storage space 15 may be sealed by the closure 13 under sterile conditions. In this way and as long as the medicament container 100 is sealed inside the packaging 10 it is stored under sterile conditions and in a sterile environment.

The container 10, at least its bottom 12 and its sidewall structure 14 as illustrated in FIGS. 2-5 is typically made of a thermoplastic material. The bottom 12 and the sidewall structure 14 may be produced by way of thermoforming, deep drawing or injection molding. In this way, a protrusion 34 of arbitrary and required shape or size can be generated. Moreover, the protrusion 34 can be integrally formed with the proximal sidewall section 18. Hence, a separate assembly of, arrangement and fixing of the protrusion 34 to the sidewall structure 14 becomes superfluous.

The protrusion 34 as illustrated in FIGS. 2 and 3 comprises a bulged and convex shaped geometry. The protrusion 34 is configured to engage or to abut with the proximal side of the bung 104. Alternatively or additionally it may also engage and abut with the proximal end of the barrel 102, hence with the proximal container abutment section 130.

Figure 4:
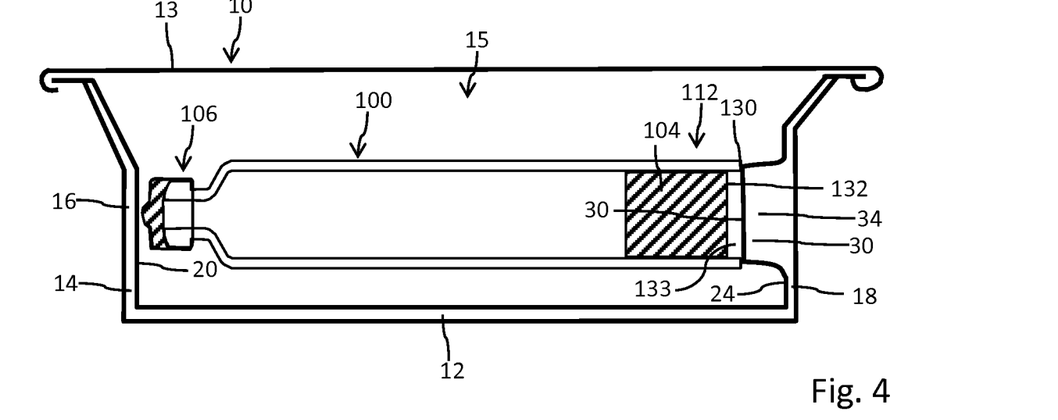
FIG. 4 shows a further example of a packaging accommodating a medicament container.

With the example of FIG. 4 the protrusion 34 comprises a cross-section or a diameter that substantially matches or is larger than a cross-section or diameter of the barrel 102 of the medicament container 100. Here, a distal abutment face of the protrusion 34 is configured to abut with the proximal container abutment section 130, hence with the proximal end of the barrel 102. The further proximal container abutment section 132 provided at the proximal end face of the bung 104 may be located distally offset from the proximal end of the barrel 102. There may be provided an axial gap 133 between the distal end face of the protrusion 34 and the proximal end face of the plunger 104. This gap defines a maximum path length along which the bung 104 may move relative to the barrel 102 in proximal direction 3 during transportation and storage. At maximum the bung 104, in particular its proximal end face may flush with the proximal container abutment section 130, hence with the proximal end of the barrel 102. Then, the gap 133 will be closed and any further proximally directed movement of the bung 104 is blocked and impeded by the protrusion 34.

Figure 6:
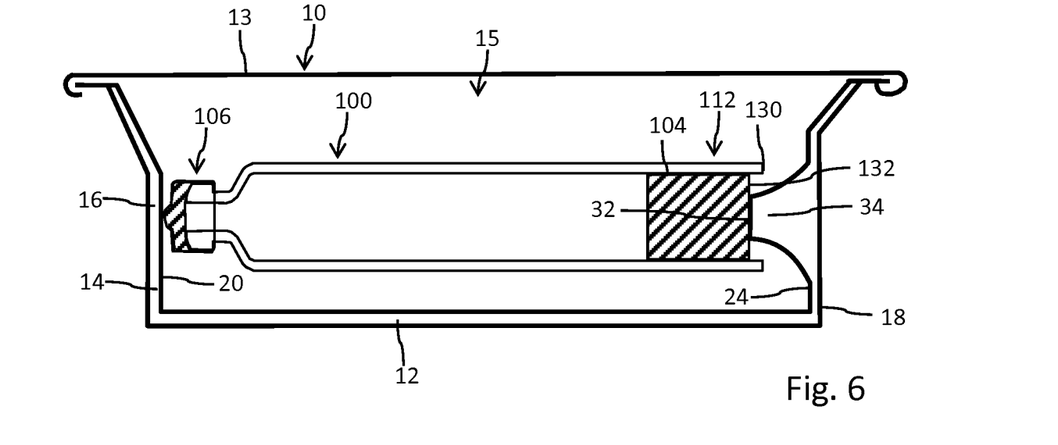
FIG. 6 shows a further example of a packaging accommodating a medicament container.

In the further example of FIG. 6 the protrusion 34 comprises a diameter or cross-section that is smaller than a respective diameter or cross-section of the barrel 102. In this way, the distal end face of the protrusion 34 can enter the proximal end of the barrel 102 in distal direction 2 and may get in direct contact or abutment with the proximal container abutment section 132 located at the proximal end of the bung 104. In this way the bung 104 is hindered to move in proximal direction 3 relative to the packaging 10 and hence relative to the barrel 102.

A movement of the barrel 102 in proximal direction relative to the bung 104 is effectively impeded because the interior of the barrel 102 is filled with a fluid being substantially incompressible. In this way, and as long as the outlet 106 is intact any force directed to the barrel 102 in proximal direction 3 relative to the bung 104 will not lead to a respective relative movement of the bung 104 inside the barrel 102.

Figure 5:
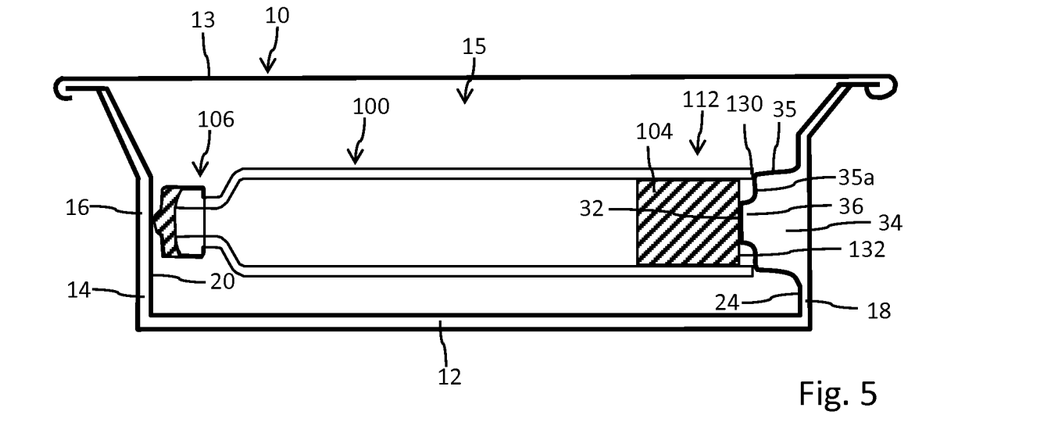
FIG. 5 shows a further example of a packaging accommodating a medicament container.

With the further example of FIG. 5 the protrusion 34 comprises a base portion 35 and a free end portion 36 as seen from the proximal direction towards the distal direction 2. The base portion 35 is connected to or integrally formed with the proximal sidewall section 18 and protrudes from the inward facing side 24 of the proximal sidewall section 18. The base portion 35 extends in distal direction 2 and merges into a narrowed or step down free end portion 36 forming the distal end of the protrusion 34. As illustrated in FIG. 5 the free end portion 36 comprises a second cross-section that is smaller than a first cross-section of the base portion 35.

The first cross-section and hence the cross-section of the base portion 35 matches with or is larger than a cross-section of the barrel 102. The cross-section of the free end portion 36 is smaller than the cross-section of the barrel 102. In this way the distal end face of the free end portion 36 is configured to abut with the proximal container abutment section 132 and the radially widened base portion 35. In particular, a widened shoulder portion 35a is configured to abut and to engage with the proximal container abutment section 130, i.e. the proximal end of the cartridge 102. In this way the protrusion 34 fulfills a double function. It engages and abuts simultaneously with the proximal end of the barrel 102 as well as with the proximal end of the bung 104.

When the proximal sidewall section 18 is provided with a protrusion 34 it is of particular benefit that the oppositely located distal sidewall section 16 comprises a slanted or beveled section 16a near or at the upper end. In this way, the container 100 can be inserted in a slightly tilted or slanted fashion into the storage space 15 from above with a lowered proximal end 112 getting in abutment with the protrusion 34 while the distal end 110 is located in the region of the beveled section 16a. Then, already a slight pressure applied from above to the distal end 110 of the container 100 may be sufficient to smoothly urge the container 100 into a final accommodating position as illustrated in FIGS. 2-6.

Figure 7:
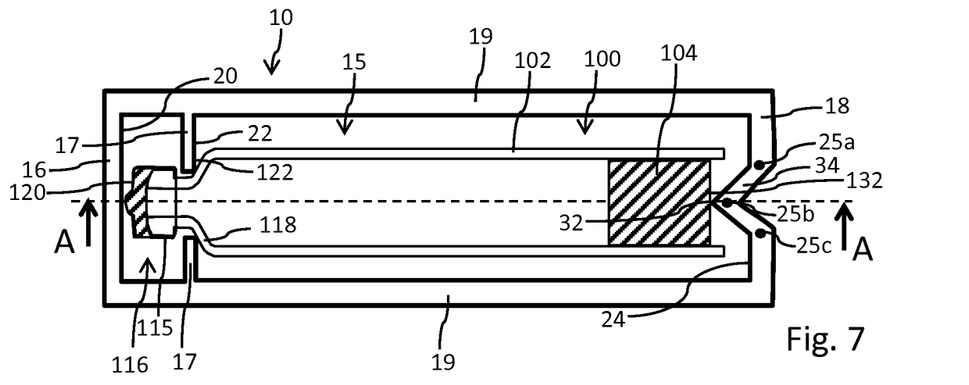
FIG. 7 is a top view of another example of a packaging accommodating a medicament container.
Figure 8:
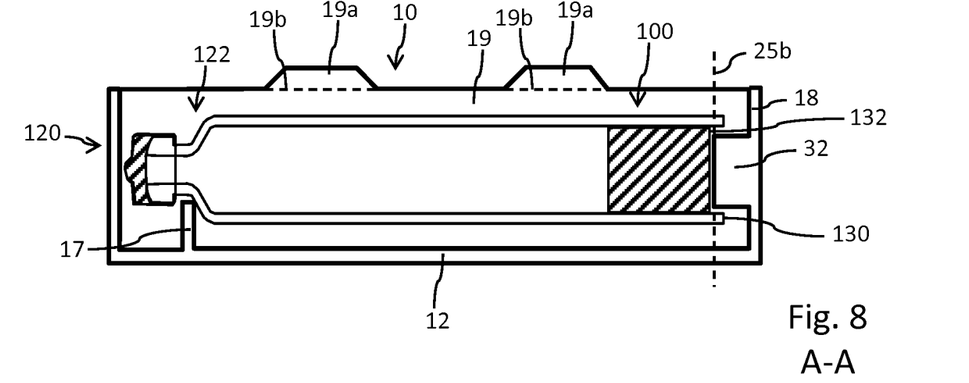
FIG. 8 is a cross-section and a side view along A-A of FIG. 7.

In FIGS. 7 and 8 a further example of a packaging 10 is illustrated. There, the proximal packaging abutment section 32 comprises a triangular-shaped inwardly facing protrusion at the proximal sidewall section 18. There is further provided a second distal packaging abutment section 22 formed by an inwardly facing flange section 17 protruding inwardly from the lateral sidewall sections 19 and/or protruding inwardly from the bottom 12 as illustrated in FIG. 8. The flange section 17 is located near the distal sidewall section 16. Between the flange section 17 and the distal sidewall section 16 there is formed a compartment sized to receive the radially widened head portion 116 of the medicament container 100.

The inwardly protruding flange portion 17 is configured to engage and to abut with the shoulder portion 118 of the barrel 102. Hence, a proximally facing abutment face of the flange portion 17 forms or constitutes the distal packaging abutment section 22 facing in proximal direction 3 and being configured to abut or to engage with the distally facing and radially widening shoulder portion 118 of the medicament container. Here, the shoulder portion 118 forms or constitutes the distal container abutment section 122. Alternative to the illustration of FIGS. 7 and 8 the flange portion 17 may also form or constitute a further distal packaging abutment section that is configured to engage with a proximal side of the beaded cap 115 at the proximal end of the head portion 116.

The proximal packaging abutment section 32 is an inwardly folded protrusion of the proximal sidewall section 18. The packaging 10, its bottom 12 and its sidewall structure 14 may comprise a foldable cardboard material. In an initial configuration the proximal sidewall section 18 may comprise at least three predefined fold lines 25a, 25b, 25c defining or coinciding with folding axes along which a portion of the proximal sidewall section 18 can be folded. In an initial configuration the protrusion 34 may comprise an outwardly folded portion, which after insertion of the medicament container 100 into the storage space 15 is foldable inwardly so as to generate a protrusion 34 protruding inwardly from the inward facing side 24 of the proximal sidewall section 18 as illustrated in FIG. 7.

As further illustrated in the side view of FIG. 8 an upper end of the lateral sidewall section 19 may comprise at least one or several fixing flap portions 19a that may be foldable across or over an upper end of the barrel 102. The fixing flaps 19a as illustrated in FIG. 8 protrude upwardly they are foldable along fold lines 19b so as to form a kind of a lid or closure to fasten the medicament container 100 inside the storage space 15.

Figure 9:
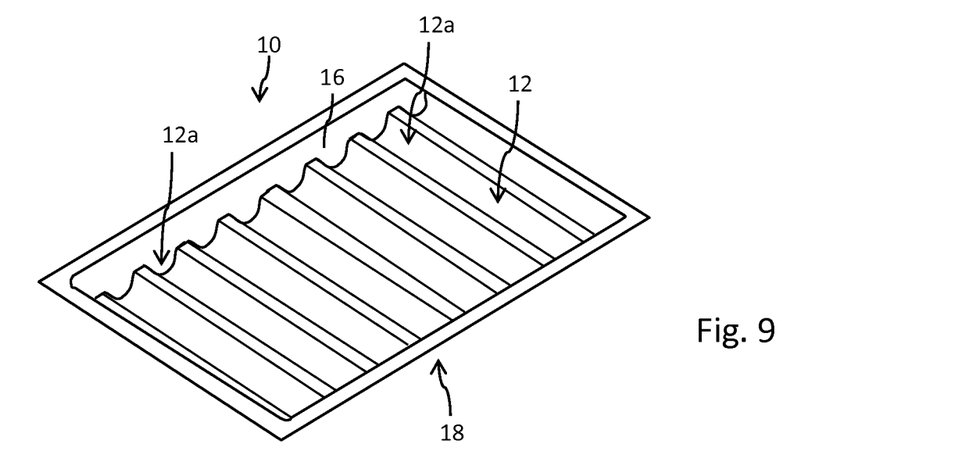
FIG. 9 is a perspective illustration of a packaging configured to accommodate a plurality of medicament containers.
Figure 10:
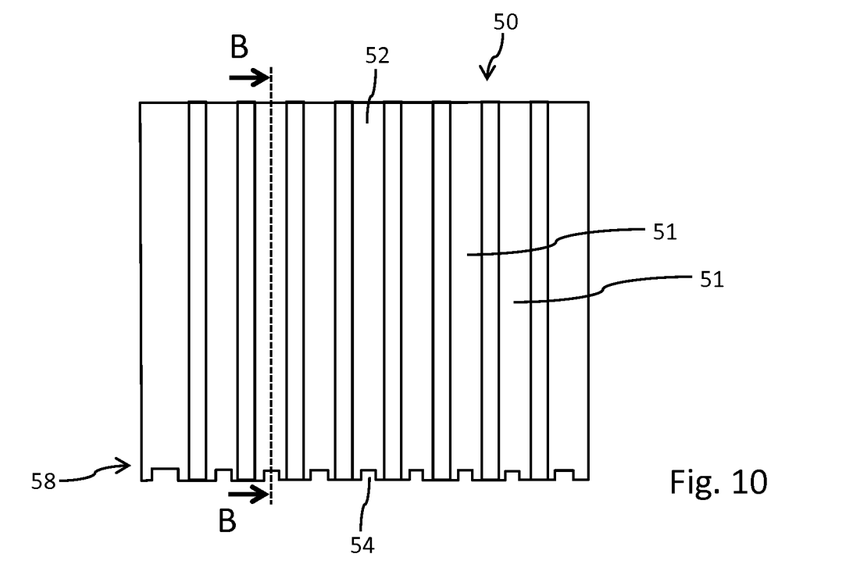
FIG. 10 is a top view of an insert configured for insertion into or onto the packaging according to FIG. 9.
Figure 11:
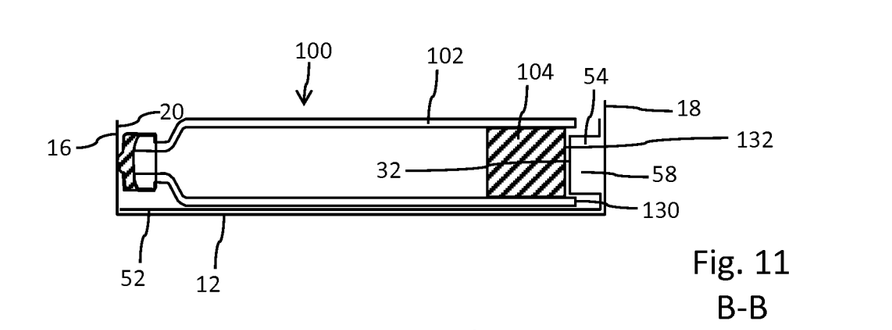
FIG. 11 is a cross-section along B-B of an insert according to FIG. 9 when arranged in or on top of a packaging of FIG. 8

The further example of FIGS. 9-11 shows another packaging 10 having a bottom 12 featuring numerous wells 12a each of which being configured to accommodate one medicament container 100. The medicament containers 100 are not illustrated in FIG. 9. There are provided numerous wells 12a arranged next to each other. The distal ends of the wells 12a are delimited by a distal sidewall section and the proximal ends of the wells 12a are delimited and confined by a proximal sidewall section 18 protruding upwardly from the plane of the wells 12a.

Here, at least one of the distal sidewall sections 16 and the proximal sidewall sections 18 are free of protrusion 34. Instead, there is provided an insert 50, e.g. in form of a planar sheet. The insert 50 comprises a bottom section 52 configured for an arrangement all across the bottom 12 of the packaging 10 as illustrated in FIG. 10. The bottom section 52 of the insert 50 is partitioned in a number of elongated sections 51 each of which adapted to the shape of a well 12a of the bottom 12. The insert 50 as illustrated in the cross-section of FIG. 11 comprises a proximal sidewall section 58 protruding upwardly from the planar bottom section 52. At the sidewall section 58 there is provided an inwardly protruding protrusion 54 as illustrated in FIGS. 10 and 11. The protrusion 54 provides a proximal packaging abutment section 32 to engage with or to abut with the proximal end of the bung 104 of the medicament container 100. The insert 50 can be attached and fixed to at least one of the bottom 12 and the sidewall structure 14.

Alternatively, the bottom section 52 of the insert 50 may comprise a longitudinal length equal to or matching with the longitudinal length of the bottom 12. In other words, a distal end of the bottom section 52 may abut with the distal sidewall section 16 and a proximal end of the bottom section 52 may abut with the proximal sidewall section 18. In this way, the bottom 52 can be fixed in longitudinal direction simply by placing the bottom section 52 of the insert 50 between the distal sidewall section 16 and the proximal sidewall section 18.

The insert 50 allows retrofitting of an existing packaging 10 for medicament containers 100. Moreover, different inserts 50 with differently shaped protrusions 54 may be provided thus providing differently shaped proximal packaging abutment sections 32 for different positions or shapes of medicament container barrels or medicament container bungs.

Figure 12:
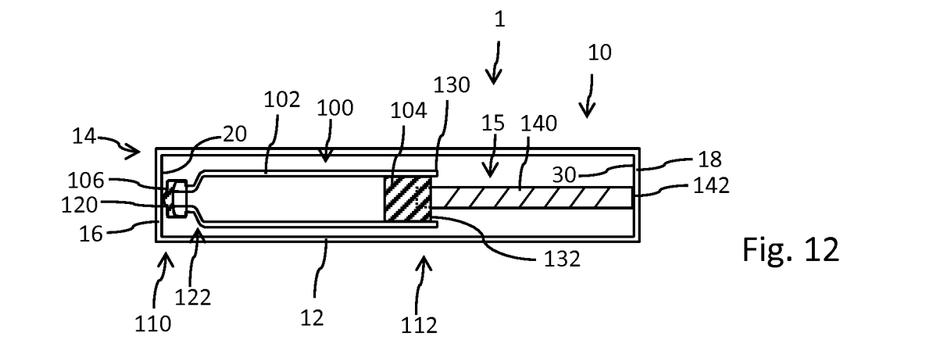
FIG. 12 shows a further example of a packaging for a medicament container, wherein the medicament container is further equipped with a plunger.

In the further example of FIG. 12 a packaging assembly 1 is illustrated. The packaging assembly comprises a packaging 10 and a medicament container 100 assembled inside a storage space 15 of the packaging 10. The medicament container comprises a barrel 102 and a bung 104. The bung 104 is arranged inside the barrel 102. The barrel 102 has an outlet 106 at a distal end 110 and the bung 104 is movably arranged inside the barrel 102 and seals the barrel 102 towards a proximal end 112. As described above the medicament container 100 comprises at least one distal container abutment section 120, 122 facing in the distal direction 2. The medicament container further comprises at least one proximal container abutment section 130, 132 facing in the proximal direction. The proximal container abutment section 130 may be provided by a proximal end 112 of the barrel 102. Alternatively, the proximal container abutment section 132 may be provided by a proximal end face of the bung 104.

The packaging 100 comprises a bottom 12 and a sidewall structure 14 connected to the bottom 12. The bottom 12 and the sidewall structure 14 confine a storage space 15 to accommodate the at least one medicament container 100. The packaging 10 further comprises at least one distal packaging abutment section 20 integrated into or arranged at the sidewall structure 14 and configured to abut with the at least one distal container abutment section 120. As illustrated in FIG. 12 the distal packaging abutment section 20 is provided by an inside of a distal sidewall section 16 of the packaging 10. The packaging 10 also comprises a proximal packaging abutment section 30 integrated into or arranged at the sidewall structure 14. As illustrated in FIG. 12 the proximal packaging abutment section 30 is provided at an inside of a proximal sidewall section 18 of the packaging 10.

The packaging assembly further comprises at least one spacer 140 arranged between the proximal packaging abutment section 30 and the proximal container abutment section 130, 132. The at least one spacer 140 is sized to bridge a gap between the proximal packaging abutment section 30 and the proximal container abutment section 130, 132.

As illustrated in FIG. 12 the spacer 140 may comprise or may conform a plunger or a piston rod preassembled to the bung 104 of the medicament container 100. The medicament container 100 may comprise a cartridge configured for use in a pen-type injector. Here, the spacer 140 may comprise or may constitute a piston rod of the pen-type injector. The piston rod may be configured for engagement with the drive mechanism 64 of an injection device 60 as illustrated in FIG. 1. Alternatively, the medicament container 100 comprises a prefilled syringe, wherein the spacer 140 comprises or constitutes a plunger depressible by a thumb of a user for expelling the medicament through the distal outlet 106 of the barrel 102.

When attached to one of the bung 104 and the barrel 100 a proximal end of the spacer 140 may be configured to engage, e.g. to abut with the proximal packaging abutment section 30. In this example, the proximal packaging abutment section 30 is provided and constituted by an inward facing side 24 of a proximal sidewall section 18 of the packaging 10. The distal container abutment section 120 is provided by the distal end 110 of the barrel, e.g. by the end of the head portion 116. The distal packaging abutment section 20 is formed and provided by the distal side wall section 16. The proximal end of the plunger 140 may also provide and constitute the proximal container abutment section 142 configured to engage with the proximal packaging abutment section 30.

The spacer 140 may be provided with an outer thread or with a longitudinal groove. The spacer 140 may be fixed to the bung 104 of the medicament container 100. The plunger 140 and the bung 104 may be also integrally formed as a single piece.

Furthermore, the spacer 140 may be provided as a separate piece configured to bridge the gap between the proximal packaging abutment section 30 and the proximal container abutment section 130, 132.

LIST OF REFERENCE NUMBERS 1 packaging assembly
2 distal direction
3 proximal direction
10 packaging
12 bottom
12a well
13 closure
14 sidewall structure
15 storage space
16 distal side wall section
16a beveled section
16b flange section
17 flange section
18 proximal sidewall section
18a beveled section
18b flange section
19 lateral sidewall section
19a fixing flap 19b fold line
20 distal packaging abutment section
22 distal packaging abutment section
24 inward facing side
25a, b, c fold line
30 proximal packaging abutment section
32 proximal packaging abutment section
34 protrusion
35 base portion
35a shoulder portion
36 free end portion
50 insert
51 section
52 bottom section
54 protrusion
58 sidewall section
60 injection device
61 body
62 cartridge holder
63 window
64 drive mechanism
65 piston rod
66 dose button
67 dose dial
68 protective cap
100 medicament container
102 barrel
104 bung
105 medicament
106 outlet
110 distal end
112 proximal end
114 seal
115 beaded cap
116 head portion
117 neck portion
118 shoulder portion
120 distal container abutment section
122 distal container abutment section
130 proximal container abutment section
132 proximal container abutment section
133 gap
140 spacer
142 proximal container abutment section

The invention claimed is:

1. A packaging including a medicament container, wherein the medicament container comprises a barrel and a bung, wherein the bung is arranged inside the barrel, wherein the barrel has an outlet at a distal end and wherein the bung is movably arranged inside the barrel and seals the barrel towards a proximal end, wherein the barrel is filled with a liquid medicament, wherein the medicament container comprises a distal container abutment section facing in a distal direction and comprises a proximal container abutment section facing in a proximal direction, wherein the proximal container abutment section is located at a proximal end face of the barrel or a proximal end face of the bung inside the barrel, the packaging comprising:
  a bottom,
  a sidewall structure connected to the bottom, wherein the sidewall structure comprises a distal sidewall section and a proximal sidewall section, wherein the distal sidewall section, the proximal sidewall section, and the bottom define a storage space configured to accommodate the medicament container, wherein the distal sidewall section and the proximal sidewall section are integrally formed with at least one of the sidewall structure or the bottom, and
  a distal packaging abutment section integrated into or arranged at one of the sidewall structure or the bottom and configured to abut with the distal container abutment section,
  wherein the sidewall structure comprises a proximal packaging abutment section configured to abut with the proximal container abutment section, and
  wherein the proximal packaging abutment section is integrated into or is arranged at an inward facing side of the proximal sidewall section and comprises a protrusion protruding from the inward facing side into the storage space.

2. The packaging according to claim 1, wherein the protrusion comprises a cross-section that is larger than or equal to a cross-section of the barrel at the proximal end of the barrel.

3. The packaging according to claim 1, wherein the protrusion comprises a cross-section that is smaller than a cross-section of the barrel at the proximal end of the barrel.

4. The packaging according to claim 1, wherein the protrusion comprises a base portion and a free end portion, wherein the base portion is located between the free end portion and the proximal sidewall section, wherein the base portion comprises a first cross-section, wherein the free end portion comprises a second cross-section and wherein the second cross-section is smaller than the first cross-section.

5. The packaging according to claim 1, wherein the protrusion comprises one of a tapered, a bulged, or a convex shaped geometry.

6. The packaging according to claim 1, wherein at least one of the sidewall structure and the bottom comprises a flange section protruding inwardly into the storage space and forming the distal packaging abutment section.

7. The packaging according to claim 1, wherein the bottom and the sidewall structure comprise a thermoplastic material.

8. The packaging according to claim 1, wherein the bottom and the sidewall structure comprise a foldable cardboard material.

9. The packaging according to claim 1, wherein the distal container abutment section is configured to abut a distal end face of the medicament container.

10. The packaging according to claim 1, wherein the distal container abutment section is located at a distally facing shoulder section of the barrel.

11. The packaging according to claim 1, wherein the proximal packaging abutment section is configured to abut the proximal end face of the barrel or the proximal end face of the bung inside the barrel.

12. The packaging according to claim 1, wherein the medicament container is arranged inside the storage space.

13. The packaging according to claim 1, wherein an effective longitudinal size of the storage space defined by a distance between the distal packaging abutment section and the proximal packaging abutment section is substantially equal to or smaller than an effective abutment size of the medicament container plus an effective insertion depth of the bung, wherein the effective abutment size is defined by a distance between the distal container abutment section and the proximal container abutment section and wherein the effective insertion depth of the bung is defined as a longitudinal distance between a distal end face of the bung and the proximal face end of the barrel.

14. The packaging according to claim 1, wherein an effective longitudinal size of the storage space defined by a distance between the distal packaging abutment section and the proximal packaging abutment section is substantially equal to or smaller than an effective abutment size of the medicament container plus a longitudinal length of the bung, wherein the effective abutment size is defined by a distance between the distal container abutment section and the proximal container abutment section.

* * * * *